United States Patent
Hilsebecher et al.

(10) Patent No.: US 10,043,074 B2
(45) Date of Patent: Aug. 7, 2018

(54) METHOD FOR ASCERTAINING THE HEART RATE OF THE DRIVER OF A VEHICLE

(71) Applicant: Robert Bosch GmbH, Stuttgart (DE)

(72) Inventors: Joerg Hilsebecher, Hildesheim (DE); Philippe Dreuw, Heersum (DE)

(73) Assignee: ROBERT BOSCH GMBH, Stuttgart (DE)

( * ) Notice: Subject to any disclaimer, the term of this patent is extended or adjusted under 35 U.S.C. 154(b) by 270 days.

(21) Appl. No.: 14/744,158

(22) Filed: Jun. 19, 2015

(65) Prior Publication Data

US 2015/0367780 A1    Dec. 24, 2015

(30) Foreign Application Priority Data

Jun. 20, 2014    (DE) .................... 10 2014 211 882

(51) Int. Cl.
| | |
|---|---|
| A61B 3/113 | (2006.01) |
| G06K 9/00 | (2006.01) |
| A61B 5/18 | (2006.01) |
| A61B 5/00 | (2006.01) |
| A61B 5/024 | (2006.01) |

(52) U.S. Cl.
CPC .......... *G06K 9/00604* (2013.01); *A61B 3/113* (2013.01); *A61B 5/0077* (2013.01); *A61B 5/024* (2013.01); *A61B 5/18* (2013.01); *G06K 9/00845* (2013.01)

(58) Field of Classification Search
CPC ................................................. G06K 9/00604
See application file for complete search history.

(56) References Cited

U.S. PATENT DOCUMENTS

| | | | | |
|---|---|---|---|---|
| 7,602,278 | B2 * | 10/2009 | Prost-Fin ............... | B60K 35/00 340/438 |
| 7,835,834 | B2 * | 11/2010 | Smith ................... | A61B 3/113 340/425.5 |
| 7,982,618 | B2 * | 7/2011 | Omi ...................... | G08B 21/06 340/573.1 |
| 8,077,915 | B2 * | 12/2011 | Thorn .................... | G06Q 10/02 382/103 |
| 8,274,578 | B2 * | 9/2012 | Hong .................... | G06F 3/013 348/222.1 |
| 8,322,855 | B2 * | 12/2012 | Gimenez ............... | A61B 3/113 351/200 |
| 8,604,932 | B2 * | 12/2013 | Breed .................... | B60J 10/00 340/576 |
| 8,754,388 | B2 * | 6/2014 | Guez ..................... | A44C 5/20 250/396 R |
| 8,849,845 | B2 * | 9/2014 | Pasquero .......... | G06F 17/30864 707/706 |

(Continued)

FOREIGN PATENT DOCUMENTS

| | | |
|---|---|---|
| DE | 102010023369 | 12/2010 |
| WO | 9849028 A1 | 11/1998 |

*Primary Examiner* — Jay Patel
*Assistant Examiner* — Irfan Habib
(74) *Attorney, Agent, or Firm* — Norton Rose Fulbright US LLP; Gerard Messina

(57) ABSTRACT

In a method for ascertaining the heart rate of the driver of a vehicle, the eye position is determined with the aid of a camera, and an image section of the driver's head is acquired. To ascertain the heart rate, successive images which were recorded over time with the aid of the camera are analyzed.

19 Claims, 2 Drawing Sheets

(56) References Cited

U.S. PATENT DOCUMENTS

| | | | | |
|---|---|---|---|---|
| 8,885,882 B1* | 11/2014 | Yin | ............ | G06F 3/00 |
| | | | | 382/103 |
| 8,986,218 B2* | 3/2015 | De Lemos | ............ | A61B 3/112 |
| | | | | 351/206 |
| 8,988,350 B2* | 3/2015 | Karmarkar | ............ | G06F 3/013 |
| | | | | 345/158 |
| 9,043,042 B2* | 5/2015 | Kalhous | ............ | G06F 3/013 |
| | | | | 701/1 |
| 9,120,379 B2* | 9/2015 | Wunsche | ............ | B60K 35/00 |
| 9,129,505 B2* | 9/2015 | Breed | ............ | G08B 21/0407 |
| 9,380,976 B2* | 7/2016 | Stack | ............ | A61B 5/162 |
| 9,542,847 B2* | 1/2017 | Sherony | ............ | G08G 1/167 |
| 9,554,185 B2* | 1/2017 | Narasimhan | ..... | H04N 21/44218 |
| 2002/0188219 A1* | 12/2002 | Suchard | ............ | A61B 5/18 |
| | | | | 600/558 |
| 2007/0291983 A1* | 12/2007 | Hammoud | ......... | G06K 9/00604 |
| | | | | 382/103 |
| 2012/0150387 A1* | 6/2012 | Watson | ............ | A61B 5/0077 |
| | | | | 701/36 |
| 2012/0195486 A1 | 8/2012 | Kirenko et al. | | |
| 2014/0276090 A1* | 9/2014 | Breed | ............ | A61B 5/18 |
| | | | | 600/473 |
| 2014/0276104 A1* | 9/2014 | Tao | ............ | A61B 5/7239 |
| | | | | 600/476 |
| 2014/0375785 A1 | 12/2014 | Kogut et al. | | |
| 2015/0379362 A1* | 12/2015 | Calmes | ............ | G06K 9/2036 |
| | | | | 348/136 |
| 2016/0110868 A1* | 4/2016 | Cheng | ............ | G06T 7/0014 |
| | | | | 382/128 |
| 2016/0342206 A1* | 11/2016 | Shazly | ............ | A61B 5/1114 |

\* cited by examiner

METHOD FOR ASCERTAINING THE HEART RATE OF THE DRIVER OF A VEHICLE

FIELD OF THE INVENTION

The present invention relates to a method for ascertaining the heart rate of the driver of a vehicle.

BACKGROUND INFORMATION

From German Published Patent Application No. 10 2010 023 369 A1 it is already known to integrate an electrode into a vehicle seat for the capacitive measurement of biological signals, so that an electrocardiogram of a vehicle passenger can be recorded in a contact-free manner. The electrode is made up of multiple electrically acting layers, which are situated directly on top of each other, are developed as sensor layer, shield layer as well as grounding layer and include interposed insulating layers. In the capacitive measurement for ascertaining the electrocardiogram, one layer of the electrodes forms the plate of an electrical plate-type capacitor, and the skin surface of the driver forms the second plate. The information from the ascertained electrocardiogram can be used for the vehicle control or be transmitted in a wireless manner to an external station.

SUMMARY

The present invention is based on the objective of ascertaining the heart rate of the driver of a vehicle with high precision.

The method of the present invention makes it possible to determine the heart rate of the driver of a vehicle in a contactless manner and with high precision. This is accomplished with the aid of a camera, which is aimed at the head of the driver and determines the eye position of the driver. The images recorded by the camera are subsequently analyzed, and multiple temporally successive images of the camera are examined in an effort to ascertain the heart rate. The analysis pertains to an image section of the driver's head, in which changes in the examined image section across the temporally successive images shed light on the heart rate of the driver.

This procedure has the advantage that the determination of the eye position makes it possible to determine the image section of the driver's head on the basis of which the heart rate is ascertained in a precise manner. As soon as the eye position has been determined, the image section of interest is likewise known very precisely, via the relative position vis-à-vis the eye position, and can then be analyzed in a subsequent evaluation on the basis of multiple successively recorded images of the camera. The ascertainment of the eye position therefore constitutes the first step, which is followed by a second step in which an ascertained image section of the driver's head is analyzed. Both the eye position and the image section to be examined for ascertaining the heart rate are preferably recorded in a joint image of the camera and analyzed.

If appropriate, the eye position can be considered in a further context as well, e.g., for ascertaining the line of sight and consequently also the head posture of the driver, which may be taken into account for instance when evaluating the attentiveness state of the driver, or for providing additional information, such as the projection of information onto the windshield. The ascertainment of the eye position therefore constitutes information that is able to be utilized multiple times in different ways.

To detect the eye position, a camera, which operates in the infrared range, and additionally perhaps also an infrared illumination device are advantageously used, via which infrared radiation, especially in the near-infrared range, is emitted in the direction of the driver. A characteristic highlight on the cornea in the region of the pupil of the driver's eye is created in that the eye reflects the infrared light in the manner of a convex mirror (corneal reflection). The highlight on the cornea is visible in the recorded image of the infrared camera, so that it can be utilized to ascertain the eye position. If appropriate, the image of the camera is able to be subjected to further image processing steps, such as a feature extraction and an ascertainment of the center of the pupil in order to ascertain the line of sight.

It is possible to create the eye position also by using light in the visible range. Here, too, a reflecting point of light is produced on the cornea of the eye, which can then be recorded by a camera operating with visible light.

An image cutaway of the camera image is analyzed in multiple successive steps in order to ascertain the heart rate. The image section contains a defined facial region, such as an eye or both eyes of the driver, or a facial region beyond the eyes, such as the lips, cheeks or the forehead. The image area including the facial region, which lies either at a specified distance from the eyes or which involves an eye or the eyes, is able to be analyzed if successive image recordings are available, for instance with the aid of an image frequency analysis method.

In the analysis, the recorded images in the image section of interest are examined either with regard to changes in color or changes in size, especially changes in volume. Because of the pulsation caused by the heart rate, the color and/or the size of the examined facial region in the image section change(s) rhythmically, which is able to be determined by the appropriate analysis methods. The heart rate results from the temporal change in color and size.

In an analysis of the eye, the eyeball in particular is examined, which pulsates in synchrony with the cardiac rhythm (fundus pulsation) and is subject to a corresponding change in color and volume, which is able to be recorded.

If appropriate, an additional detection method may be used for determining the head position, so that higher reliability of the information and the data obtained with the aid of the camera is able to be achieved. If the additional detection method does not supply an unambiguous signal, the information obtained from the camera may possibly be discarded, at least with regard to the heart frequency analysis, so that such an analysis is dispensed with. The additional detection system is used to determine the head position, for example. The detection system may also be developed as voice detection system, which is employed to ascertain whether the driver is talking. This is utilized for determining the direction of the voice origin, for instance, in order to infer the position of the driver's mouth.

The information regarding the heart rate is able to be used further in the vehicle, for instance in a driver assistance system, which is parameterized as a function of the heart rate. For example, if a heart rate suggests that the driver's health status is compromised, it may be advantageous to implement a parameterization in a driver assistance system at reduced trigger thresholds, such as in a brake assistant. In addition, it is also possible to make the information available in the vehicle in an optical, acoustic or haptic manner. Finally, the heart rate may also be transmitted to an external location, outside of the vehicle, for instance to an emergency hotline.

The method is advantageously executed in a system in the vehicle which includes a camera for ascertaining the eye position of the driver, and an evaluation unit for analyzing a recorded image section of the driver's head. The camera, for example, is an infrared camera, which may be equipped with an illumination unit, preferably for generating infrared radiation, especially in the near-infrared range.

DETAILED DESCRIPTION

Figure 1:
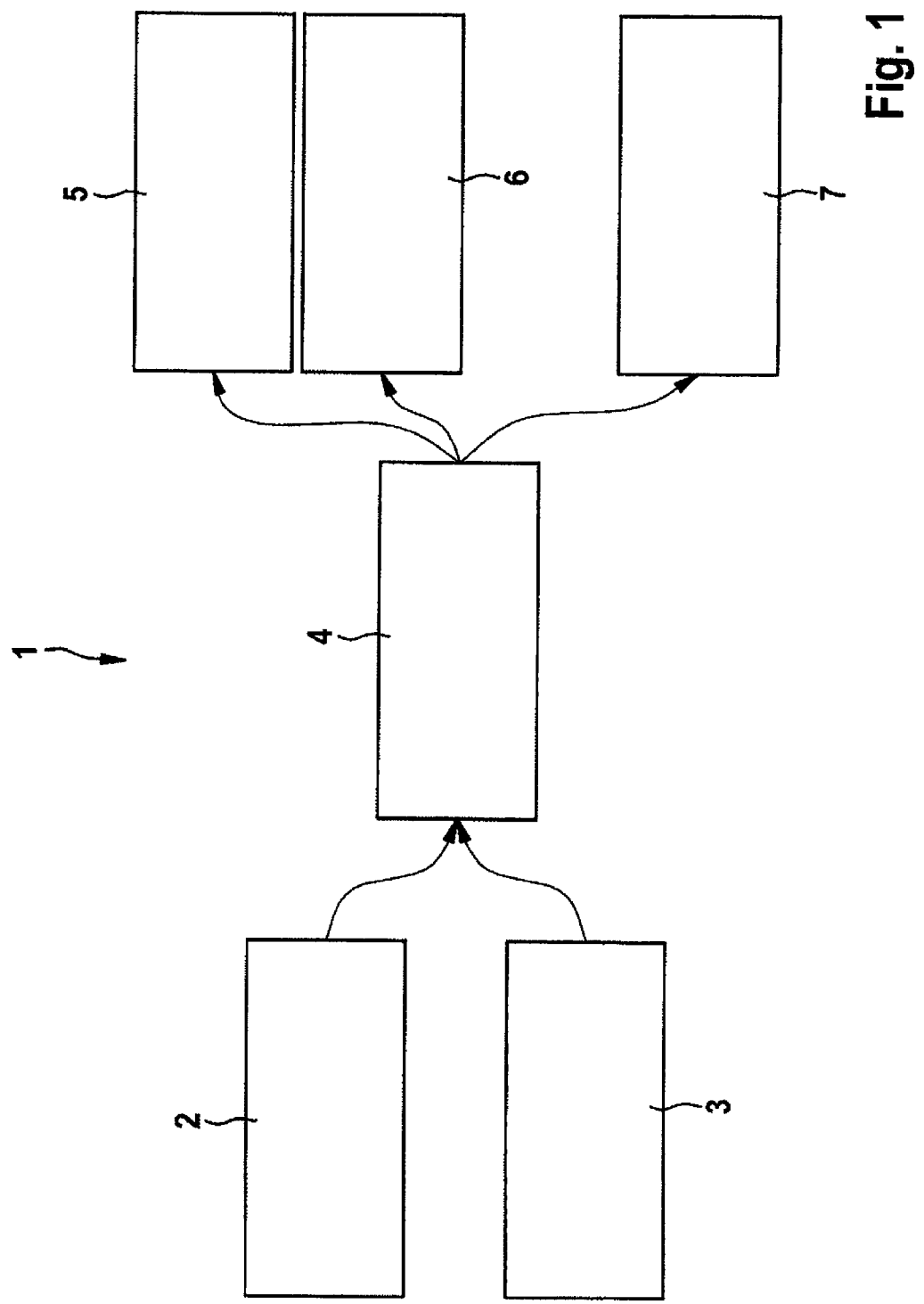
FIG. 1 shows a schematic illustration of a system for ascertaining the heart rate of the driver in a vehicle.

FIG. 1 shows a system 1 for ascertaining the heart rate of the driver in a vehicle. System 1 is installed in a vehicle and makes it possible to record the head region of the driver with the aid of one or more camera(s), and furthermore to ascertain the heart rate on the basis of the analysis of multiple successive images recorded by the camera.

System 1 includes at least one camera 3, which operates in the near-infrared range, in particular, and furthermore an additional detection system 2, which includes at least one passenger compartment sensor, with the aid of which the driver or an utterance or a reaction of the driver is able to be detected, independently of and additionally to camera 3, in an acoustic, haptic or optical manner. Detection system 2, for example, is a microphone in the vehicle interior for recording the utterances made inside the vehicle. It is advantageous that the source of the words is able to be detected with the aid of detection system 2, that is to say, the position of the driver's head, especially of the driver's mouth.

Camera 3, which preferably operates in the near infrared range, may be part of a gaze detection device, which is used to ascertain the driver's line of sight.

Camera 3 may be assigned an infrared source, such as an LED, for generating a weak infrared signal, which is reflected by the eye of the driver and recorded in the infrared-sensitive camera. In so doing, the corneal reflex in the eye is recorded by the camera, from which the eye position of the driver is inferred.

System 1 additionally includes a processing and evaluation unit 4, in which the data are analyzed and the output signals for actuating display devices 5, 6 and 7 are generated. Display devices 5, 6 and 7 preferably are optical, acoustic and/or haptic display devices for representing the heart rate of the driver ascertained in computer and evaluation unit 4. In addition or as an alternative to a display device, an actuation of a driver assistance system in the vehicle via computer and evaluation unit 4 is conceivable as well. For example, given a raised heart rate, which indicates an indisposition or an acute risk state of the driver, the parameterization of a driver assistance system, such as a brake assistant, for instance, may be changed in favor of lower trigger thresholds.

The current heart rate of the driver is determined by analyzing multiple successive images, which are recorded with the aid of camera 3 in system 1. In the process, a certain part of the driver's head is examined and analyzed, preferably an eye or both eyes of the driver, while other head regions, especially facial regions such as lips, cheeks or the forehead may be considered as well, as the case may be. The pulsation in the body induces a color and/or size in the examined facial regions that varies with the heart rate, which can be ascertained by analyzing the successive images. For example, the fundus pulsation, i.e., the change in the size of the eye, is examined and analyzed in order to ascertain the heart rate. To do so, the recorded images may be analyzed using the image frequency analysis method.

Figure 2:
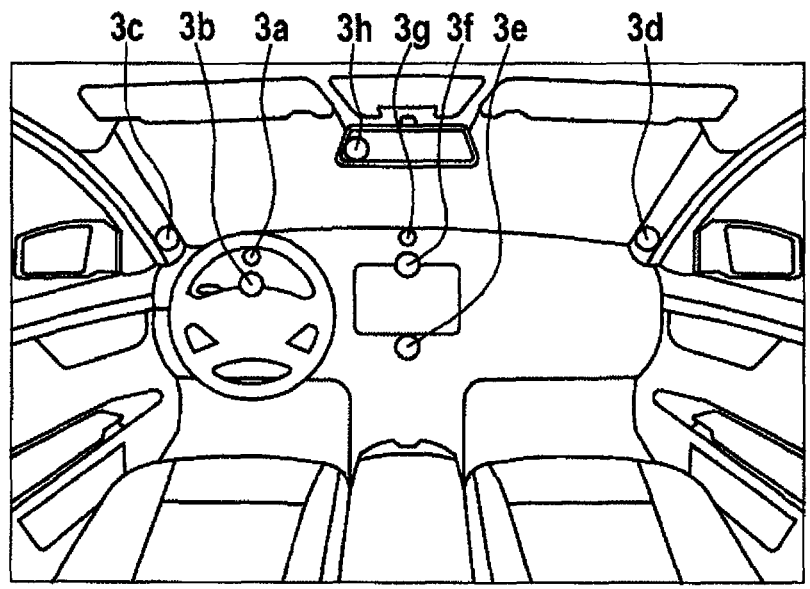
FIG. 2 shows in a perspective view, the passenger compartment of a vehicle having cameras at different positions for recording the head region of the driver.

FIG. 2 illustrates the vehicle interior of a vehicle in which cameras 3, which are part of a system for ascertaining the heart rate of the driver, have been installed at different positions. A first camera 3a is located in the dashboard area, directly below the steering wheel. A camera 3b is situated on the steering wheel, and further cameras 3c and 3d are located in the left and right A-column, respectively. Cameras 3e, 3f and 3g are disposed at different heights in the center of the dashboard area. Camera 3a is integrated into the interior mirror.

It basically suffices to provide only one camera 3 in the passenger compartment, which is focused on the head of the driver. However, it may be advantageous to provide a plurality of cameras 3 in the passenger compartment, in order to be able to record the eyes of the driver at different head positions, and to be able to derive the heart rate on this basis.

Figure 3:
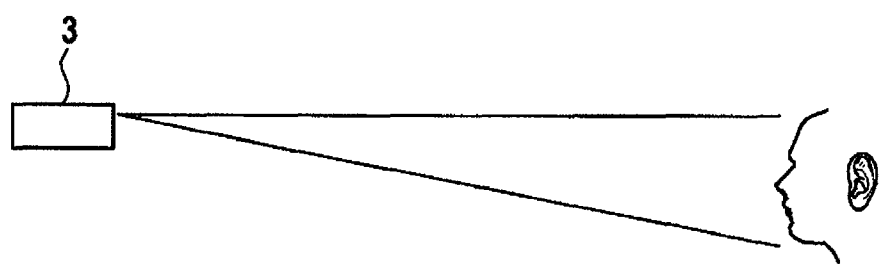
FIG. 3 shows a schematic representation of an infrared-sensitive camera for detecting the head region of the driver.

As can be gathered from FIG. 3, the orientation of camera 3 with respect to the head of the driver is such that the facial region in the eyes is able to be recorded. Using an infrared illumination unit, which may be integrated into camera 3, the driver's eye is illuminated, and the corneal reflex in the eye is recorded via the camera, from which the eye position of the driver is ascertained in a very precise manner. By recording multiple successive images with the aid of camera 3, which cover a time interval of multiple heartbeats, the heart rate, especially in the frequency range, is able to be determined by way of analysis, for instance on the basis of the fundus pulsation.

What is claimed is:

1. A method for ascertaining a heart rate of a driver of a vehicle, comprising:
    recording, via a camera, a plurality of successive images;
    analyzing, by processing circuitry, at least one of the plurality of successive images to ascertain an eye position of an eye of the driver in the plurality of successive images;
    based on the ascertained eye position, selecting, by the processing circuitry, a respective subsection within each of the plurality of successive images that corresponds to a particular subsection of a head of the driver, wherein the subsection is of the eye or is of a region that is defined by a predetermined spatial relationship to the eye;
    identifying, by the processing circuitry, differences between the subsections with respect to at least one of a size and a color of the respective subsections of the respective images of the plurality of successive images; and
    based on the identified differences, the processing circuitry ascertaining the heart rate.

2. The method as recited in claim 1, wherein the eye position of the driver is ascertained based on a corneal reflex in the eye.

3. The method as recited in claim 1, wherein the subsection of the head is of the eye.

4. The method as recited in claim 1, wherein the subsection of the head is a defined facial region outside of the eye.

5. The method as recited in claim 4, wherein the defined facial region includes lips.

6. The method for ascertaining a heart rate of a driver of a vehicle as recited in claim 5, further comprising:
using an additional detection system, which ascertains whether the driver is speaking, for increasing a reliability of information obtained by the analyzing of the camera images.

7. The method as recited in claim 1, wherein the differences are with regard to color.

8. The method as recited in claim 1, wherein the differences are with regard to size.

9. The method as recited in claim 1, wherein the recorded images are analyzed using an image frequency analysis method.

10. The method as recited in claim 1, wherein a line of sight of the driver is ascertained from the eye position.

11. The method as recited in claim 1, wherein the camera includes an infrared camera.

12. The method as recited in claim 1, wherein the camera operates in a near-infrared range.

13. The method as recited in claim 11, wherein an infrared illumination unit is used, via which infrared radiation is generated.

14. The method as recited in claim 1, further comprising using an additional detection system for increasing a reliability of information obtained by analyzing the camera images.

15. The method as recited in claim 14, wherein the additional detection system ascertains whether the driver is speaking.

16. The method as recited in claim 1, further comprising determining a pulsating pattern in the differences, the differences being with respect to color, wherein the ascertainment of the heart rate is based on the determined pulsating pattern.

17. The method as recited in claim 1, further comprising determining a pulsating pattern in the differences, the differences being with respect to size, wherein the ascertainment of the heart rate is based on the determined pulsating pattern.

18. The method as recited in claim 1, wherein the eye position of the driver is ascertained by finding in the at least one of the plurality of successive images a match to a predetermined light reflection pattern.

19. A system for a vehicle for ascertaining a heart rate of a driver, comprising:
a camera; and
an evaluation unit;
wherein the evaluation unit is configured to:
obtain, using the camera, a plurality of successive images;
ascertain an eye position of an eye of the driver in the plurality of successive images;
based on the ascertained eye position, select a respective subsection within each of the plurality of successive images that corresponds to a particular subsection of a head of the driver, wherein the subsection is of the eye or is of a region that is defined by a predetermined spatial relationship to the eye;
identify differences between the subsections with respect to at least one of a size and a color of the respective subsections of the respective images of the plurality of successive images; and
based on the identified differences, ascertain the heart rate.

* * * * *